(12) United States Patent
Fletcher

(10) Patent No.: US 8,257,341 B1
(45) Date of Patent: Sep. 4, 2012

(54) INFERIOR ALVEOLAR NERVE BLOCK GUIDE

(76) Inventor: Jack Maurice Fletcher, Brentwood, TN (US)

( * ) Notice: Subject to any disclaimer, the term of this patent is extended or adjusted under 35 U.S.C. 154(b) by 375 days.

(21) Appl. No.: 12/127,125

(22) Filed: May 27, 2008

(51) Int. Cl.
*A61M 31/00* (2006.01)

(52) U.S. Cl. ........ 604/512; 604/506; 604/116; 604/117; 433/72; 433/74; 433/76; 433/172

(58) Field of Classification Search .............. 604/77, 604/79, 131, 117, 512–514, 116, 506; 433/74–76, 433/172–176, 72; 606/96
See application file for complete search history.

(56) References Cited

U.S. PATENT DOCUMENTS

| | | | |
|---|---|---|---|
| 1,328,459 A | | 1/1920 | Smith |
| 2,317,648 A | * | 4/1943 | Siqveland ................ 433/80 |
| 3,279,122 A | | 10/1966 | Slayton |
| 3,344,525 A | * | 10/1967 | Harris ..................... 433/50 |
| 3,577,853 A | * | 5/1971 | Roberts ................... 433/176 |
| 3,738,004 A | * | 6/1973 | Edelman .................. 433/176 |
| 5,769,856 A | | 6/1998 | Dong et al. |
| 6,075,059 A | * | 6/2000 | Reader .................... 514/738 |
| 6,347,940 B1 | * | 2/2002 | Gordils Wallis ......... 433/72 |
| 7,097,451 B2 | * | 8/2006 | Tang ....................... 433/76 |

* cited by examiner

*Primary Examiner* — Bhisma Mehta
*Assistant Examiner* — Edelmira Bosques
(74) *Attorney, Agent, or Firm* — Waddey & Patterson, P.C.; Ryan D. Levy

(57) ABSTRACT

A guide for administering an injection including a guide body contoured for a human mandible; and at least one needle indexing guide on the guide body for the insertion of a needle there through, the guide use to provide a predictable and repeatable way of administering an injection to block a nerve.

19 Claims, 4 Drawing Sheets

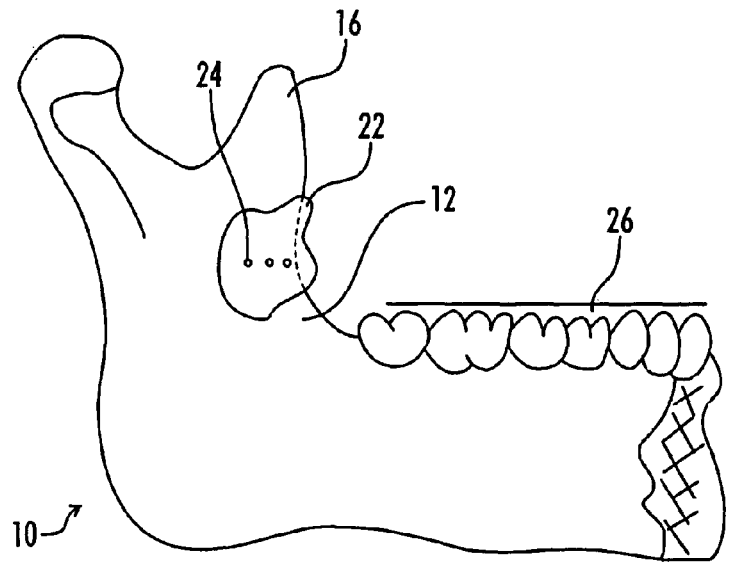
FIG. 3a
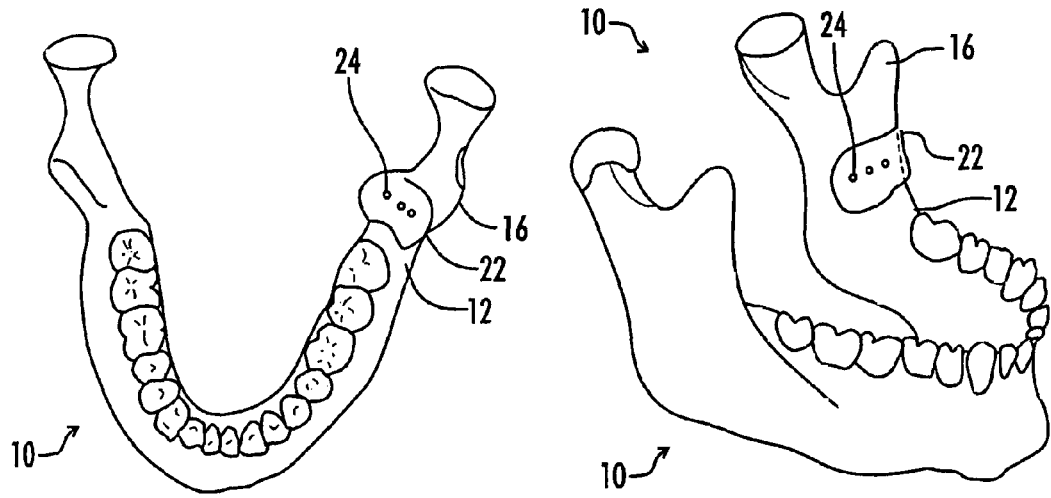
FIG. 3b  FIG. 3c

INFERIOR ALVEOLAR NERVE BLOCK GUIDE

BACKGROUND OF THE INVENTION

Technical Field

The present invention relates to the practice of oral medicine, including dentistry and is useful for applications including administering a medicament to an individual. More particularly, the present invention relates to a nerve block guide to provide a predictable and repeatable way of administering an injection to an individual. The invention also includes the method of using the inventive guide to provide an injection.

BACKGROUND OF THE ART

Dentistry is generally understood to include the evaluation, diagnosis, prevention and treatment of diseases and other medical conditions associated with the oral cavity and structures there within. Dentistry and oral medicine may include the use of X-rays, drugs, extractions, and other treatments in maintaining the dental health of an individual. One such aspect of the practice mandates the administration of medication used to anesthetize various locations within a patient's oral cavity so that procedures may be performed with little or no discomfort. For example, in Smith, U.S. Pat. No. 1,382,495, an instrument for producing intra-osseous anesthesia is disclosed. Generally, the '495 patent provides an instrument to assist in producing intra-osseous anesthesia which may include a tubular guide or a template having a sharp inner end. With such an invention, different medicaments may be injected into the intra-osseous area of a patient and providing anesthesia and is very invasive U.S. Pat. No. 2,317,648, Siquenland, discloses both a process and apparatus for producing intra-osseous anesthesia, which may include a drill and a hypodermic needle so that the hypodermic needle may be guided into the bone. Generally, the '648 patent necessitates the piercing of the patient's bone in providing the anesthesia.

In Slayton, U.S. Pat. No. 3,276,122, a position device is disclosed to position a veneer tooth on a drill press for drilling retention holes into the lingual surface of the tooth. Additionally, the '122 patent discloses a shellac cup and a flat tooth receiving surface in better assisting and positioning the veneer tooth in the proper arrangement.

Dong et al., U.S. Pat. No. 5,769,856, discloses a drill guide and implant method which facilitates the location of drilling of holes in the bone of the patient for the seating and placement of a prosthetic implant. As such, the '856 patent discloses a guide with drilling holes designed so that the prosthetic may be placed in the appropriate position.

U.S. Pat. No. 6,347,940 discloses an instrument and includes a process to verify the distance between teeth for the placement of one or two bone integrated cylinders for screw-type implants. More specifically, the '940 patent includes specific sizes so that implant may be placed at an appropriate arrangement.

In Tang, U.S. Pat. No. 7,097,451, a template is disclosed for performing dental implants osteotomies. Otherwise stated, the '451 patent is useful in implanting a prosthetic tooth by providing and fabricating a template which may be created directly within a patient's mouth to provide for greater ease in performing the operation while cutting expenses.

Unfortunately, dental devices produced by the prior art fail to assist in the administration of local anesthesia within the oral cavity and not at the intra-osseous' location. The prior art devices generally do not assist in providing injections so that specific nerves may be the target so that failure rate and undesired numbness is diminished. In addition, the prior art fails to provide a procedure for providing a predictable and repeatable method of injecting anesthesia into a patient.

What is desired therefore, is a nerve block guide which provides for a predictable and repeatable method of administering a medicament, including an anesthesia to a patient. Further desired is a method of administering an anesthesia via injection to a precise location within the oral cavity of a patient. Indeed, a combination of characteristics including assistance in targeting the inferior alveolar nerve has been found to be necessary for improving the predictability and repeatability of administering anesthesia to patients during dental applications. Also desired is a method of administering anesthesia more precisely.

SUMMARY OF THE INVENTION

The present invention provides a guide which is uniquely capable of assisting in administering injections at a precise location in applications such as dentistry. The inventive guide generally comprises a nerve block guide to provide a combination of predictability and repeatability in administering injections during dentistry to provide characteristics and safety not heretofore seen. In addition, the nerve block guide with a combination of sizing and designed orifices provide a nerve block guide which may be used for a variety of different patients in providing injections in the vicinity of the inferior alveolar nerve within the oral cavity of a patient. More particularly, the inventive nerve block guide has a design to provide a predictable way of injecting anesthesia to block the inferior alveolar nerve.

Generally, the nerve block guide is sized so as to position the needle of a hypodermic syringe at a specific location to the inferior alveolar nerve so that the nerve is numbed during dental procedures. As such, a characteristic of the nerve block guide is at least one orifice opening or slot so that a needle may be positioned at a preferable location within the oral cavity. For such applications, the nerve block guide helps to preclude the inadvertent numbing of major nerves other than the inferior alveolar nerve and also helps to preclude the inadvertent puncturing of blood vessels. Furthermore, the nerve block guide provides for greater ease in administering injections to a patient therefore allowing for the use of less medication which is much safer for the patient. Generally, an increase in the amount of anesthesia administered to the patient increases the adverse effects the patient experiences. Medical professionals must maintain the total dosage below the dosage corresponding to the toxicity level for the selected anesthesia. As only a few erroneous injections could elevate the dosage received by the patient to an unsafe level, the nerve block guide of the present invention is desirable as it substantially eliminates the occurrences of erroneous injections in numbing the inferior alveolar nerve.

The inventive nerve block guide should have a guide body shaped so that it may be placed along the anterior border of the ramus of the mandible of the patient. More specifically, the nerve block guide may have a body shaped so as to fit about the anterior border of the ramus of the mandible in the most concave curve leading to the coronoid process, referred to as the coronoid notch. Advantageously, the nerve block guide may be used to depress the pterygo-mandibular raphe and other loose tissue so as to better stabilize the tissue and provide for an improved surface within the oral cavity for the injection.

The nerve block guide provides a practitioner more control over the tissue, better sight reference as to where to place the injection, and makes the location of features along the mandible within the oral cavity more predictable. As such, the nerve block guide may simplify the needle insertion and guide the needle to the mandibular foramen location providing for a safer injection for the patient.

Advantageously, through use of the nerve block guide of the present invention, a more predictable, less traumatic application of anesthesia may result while precluding administration of the anesthesia to non-desired locations.

An object of the invention is a nerve block guide having characteristics which enable it to be employed in a variety of dental applications.

Another object of the invention is a nerve block guide sized to perform an inferior alveolar nerve block for applications including dental applications.

Still another object of the invention is a nerve block guide having at least openings for the passage of a needle therethrough for the administration of anesthesia to the inferior alveolar nerve.

Yet another object of the invention is a nerve block guide which may be readily usable for a variety of different patients for administering anesthesia in dental applications.

Another object of the invention is a method of performing an inferior alveolar nerve block with a higher degree of repeatability and predictability.

These aspects and others that will become apparent to the artisan upon review of the following description can be accomplished by providing a nerve block guide, specifically an inferior alveolar nerve block guide for the administration of an anesthesia to the inferior alveolar nerve. The inventive nerve block guide advantageously provides for a greater success rate in administering anesthesia to a patient so that a variety of dental operations and procedures can be performed.

Preferably, the nerve block guide allows for the proper depth of needle insertion in a range of from about 20 mm to about 25 mm, and more preferably of from about 20 mm to about 23 mm. Furthermore, in various embodiments of a nerve block guide, the nerve block guide may include various apertures functioning as needle guides which may span a distance on the surface of the nerve block guide from to accommodate variances in size and deviations of the mandible of different patients.

The inventive nerve block guide can be utilized with a method of administering anesthesia to a patient to perform dental procedures. The nerve block guide should preferably provide for greater control over the tissue and better sight reference as to where to place the injection on the patient.

It is to be understood that both the foregoing general description and the following detailed description provide embodiments of the invention and are intended to provide an overview of framework of understanding to nature and character of the invention as is claimed.

BRIEF DESCRIPTION OF THE DRAWINGS

FIG. 3a comprises an interior side view of one embodiment of the nerve block guide of the present invention in relation to a mandible.

FIG. 3b comprises a top view of one embodiment of the nerve block guide of the present invention in relation to a mandible.

FIG. 3c comprises a side perspective view of one embodiment of a nerve block guide of the present invention in relation to a mandible.

DETAILED DESCRIPTION OF THE PREFERRED EMBODIMENTS

Prior to a discussion of the nerve block guide of the present invention, a brief review of the anatomical features of a human jaw will assist in describing the application of the present invention. The inferior alveolar nerve is defined as a branch of the mandibular nerve which is the third branch of the trigeminal nerve. Generally, the mandibular nerve is responsible for sensory and motor function with the inferior alveolar nerve supplying dental nerves to the teeth.

Figure 1:
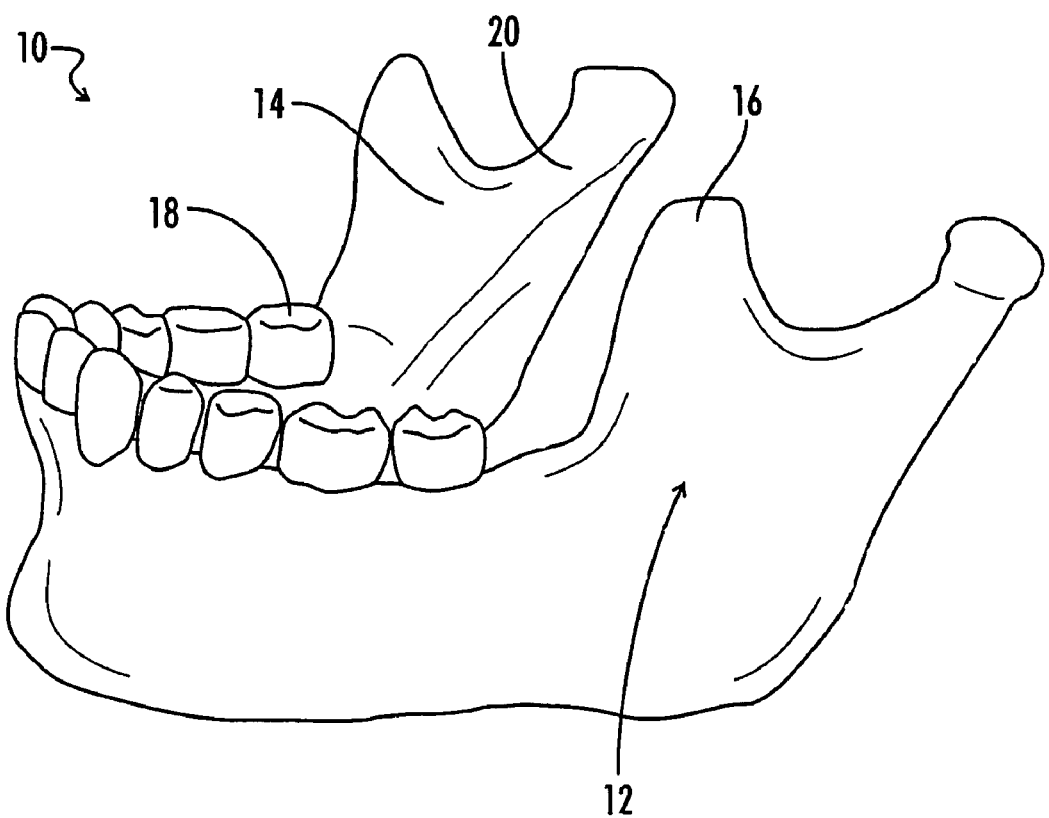
FIG. 1 comprises an illustration of a mandible of a human.

Referring now to FIG. 1, there is at 10 a mandible of a human. Generally, mandible 10 includes ramus 12 which is generally quadrilateral in shape including a lateral flat surface and a medial surface for the entrance of the inferior alveolar nerve with a medial surface designated by numeral 14. The coronoid process designated by numeral 16 is relatively triangular in shape and presents a ridge beginning near the apex of the process running toward the inner side of the last molar tooth designated by numeral 18. Mandibular foramen 20 on the internal surface of ramus 12 provides an ideal location for administering anesthesia to a patient.

In prior techniques in performing an inferior alveolar nerve block, defined as administering anesthesia to the inferior alveolar nerve to provide numbness, less painful dental procedures involve using coronoid process 16 as a landmark and a pterygo-mandibular raphe as landmarks to approximate the location of the inferior alveolar nerve. The pterygo-mandibular raphe is a tendonous band of tissue attached to the interior portion of the mandible. Generally, prior art techniques target the nerve prior to entering the foramen at a depth of about 20 to 25 mm within the vicinity of the inferior alveolar nerve. Unfortunately, with these prior techniques, clinical failure rate is significant due to anatomical variations as well as the prevalence of soft tissue and the difficulty in placing the needle in the exact location in administering the anesthesia. Problematically, deposition of the anesthesia too low or too interiorly may result in excessive numbness of other nerves within the oral cavity. Further complications may include hematomas as well as at least partial facial paralysis resulting from the misplacement of the anesthesia.

In an ideal scenario, the anesthesia is administered near the mandible foramen 20 to cause blockage of the nerve and the nearby lingual nerve for subsequent dental procedures. Unfortunately, this technique has proven difficult as the existence of soft tissue as well as small space to work, combined with various anatomical variations result in multiple attempts, more medication and greater discomfort to the patient in attempting to block the inferior alveolar nerve as well as significant difficulty for the operating dentist.

The nerve block guide in accordance with the present invention provides for a significantly greater success rate in administering anesthesia to block the inferior alveolar nerve as well as provide for a predictability and repeatability in performing this dental procedure.

Figure 2A:
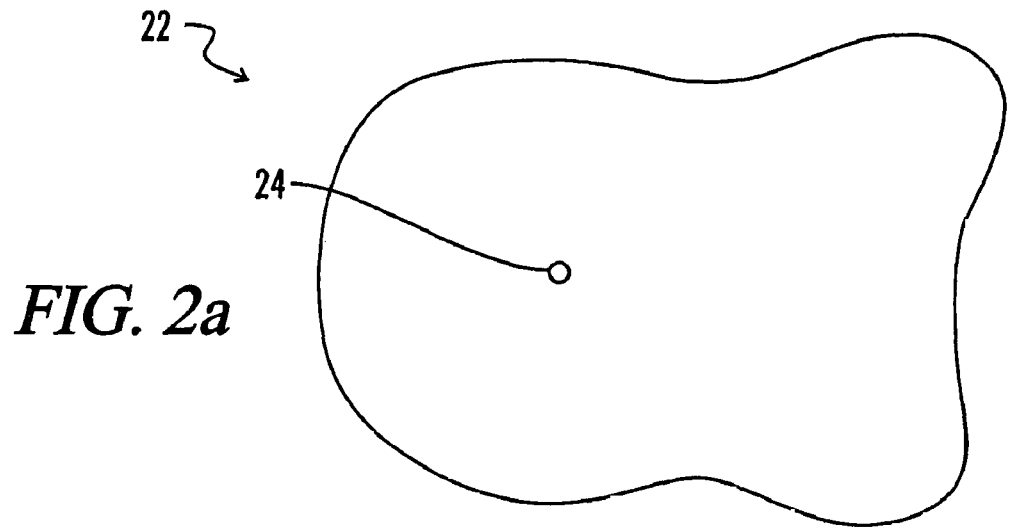
FIG. 2a comprises an illustration of one embodiment of the nerve block guide of the present invention.
Figure 2B:
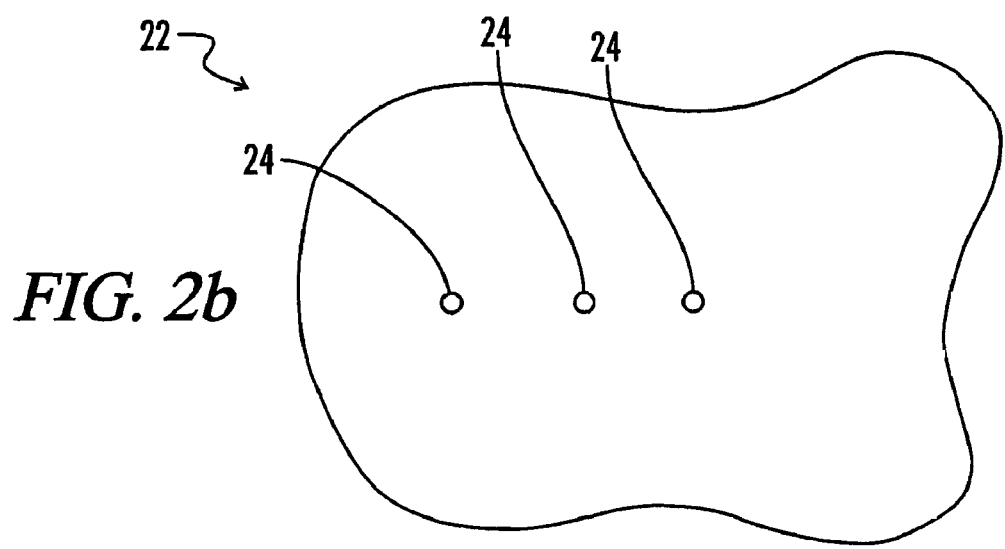
FIG. 2b comprises an illustration of one embodiment of the nerve block guide of the present invention.
Figure 2C:
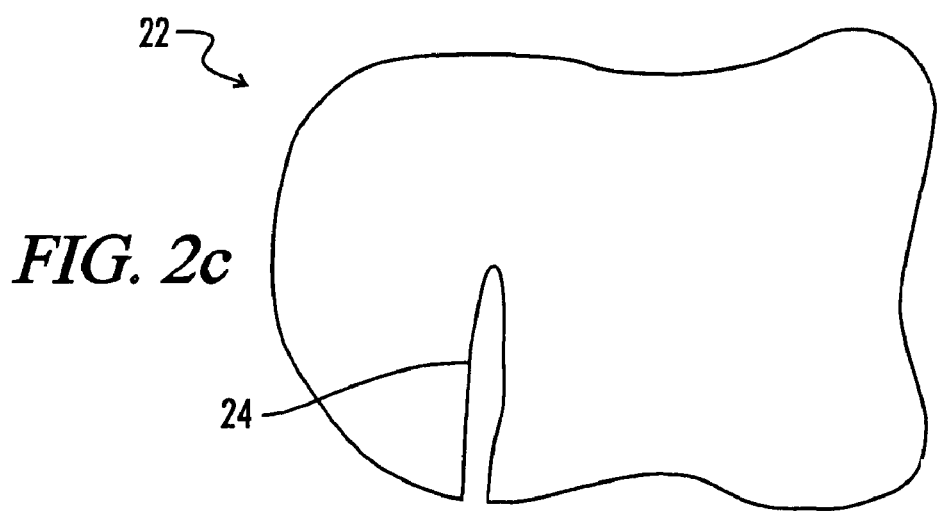
FIG. 2c comprises an illustration of one embodiment of the nerve block guide of the present invention.

Referring now to FIGS. 2a through 2c, there are multiple embodiments of the nerve block guide in accordance with the present invention. Generally, nerve block guide 22 includes a body and at least one needle indexing guide 24 which may be shaped as an orifice, slot or various size openings so that a needle may pass through nerve block guide 22 in using the invention with a patient. As further illustrated in FIG. 2b, multiple needle indexing guides 24 may be present so that the practitioner may chose an insertion site about parallel to the occlusal plane of the lower dental arch which allows for the proper needle insertion depth in administering anesthesia to the inferior alveolar nerve of the patient. Generally, the inventive nerve block guide has a curved shape only sized to the anterior border of ramus 12, preferably about the concave curve leading to coronoid process 16 referred to as the coronoid notch.

Nerve block guide 22 may be comprised of a variety of different materials including polymers, plastics, thermoplastics, metals, alloys, and combinations thereof so that the device may either be reusable or disposable upon the use with a patient. In further embodiments, nerve block guide 22 may include numbers designating the distance between different needle indexing guides 24 so that the practitioner knows the approximate distance between the spacing of multiple needle indexing guides 24. Preferably, multiple needle indexing guides 24 are positioned on nerve block guide 22 with the distance between the two farthest apart needle indexing guides being from about 10 mm to about 15 mm apart, and more preferably from about 12 to about 13 to about 14 mm apart. The spaced multiple needle indexing guides 24 help to accommodate variations in size and deviations of mandibles 10 of various patients for the medical professional to administer an anesthesia precisely.

Referring now to FIGS. 3a through 3c, there are multiple orientations of mandible 10 with nerve block guide 22 of the present invention positioned so that a user may use nerve block guide 22 to administer anesthesia to a precise location in performing an inferior alveolar nerve block. As such, one may utilize a standard accepted protocol in administering an injection with much greater precision and repeatability as nerve block guide 22 provides for a much improved control over the tissue and actual injection point of the needle used to penetrate and administer the anesthesia. Preferably, nerve block guide 22 of the present invention is sized to fit along the anterior border of ramus 12 of mandible 10 in the curve leading to the coronoid process 16. More preferably, nerve block guide 22 is contoured to fit within the most concave curve leading to coronoid process 16. By positioning nerve block guide 22, the pterygo-mandibular raphe is depressed, thus stabilizing the tissue there beneath and providing nerve index guides 24 at the proper location so as to provide a precise insertion point of a needle therethrough in administering anesthesia to the inferior alveolar nerve area. Generally, the needle is inserted through the appropriate needle index guide 24 within the body of nerve block guide 22 to allow insertion at mandibular foramen 20. Generally, anesthesia can then be deposited at the point prior to inferior alveolar nerve entering mandibular foramen 20. As such, nerve block guide 22 may provide greater control over the tissue, more improved sight reference as to where to locate the injection, and furthermore, may provide for a greater repeatability in reaching the proper injection location.

In accordance with the present invention, needle index guides 24 are positioned so that upon proper placement of nerve block guide 22, the needle indexing guides are about in a parallel plane with occlusal plane 26 of the teeth as represented by the parallel line above the teeth in FIG. 3a. In embodiments where either slots are utilized or where only one orifice is included on nerve block guide 22, a parallel plane may not be established. Regardless, nerve block guide 22 provides for a needle injection of from about 20 mm to about 25 mm and more preferably of from about 20 mm to about 23 mm in administering anesthesia to block the inferior alveolar nerve. Generally, nerve block guide 22 has a width of about 15 mm to about 22 mm and more preferably of about 18 mm with a length of from about 15 mm to about 20 mm and more preferably about 18 mm though obviously may have different variations in width or length depending on the exact design of the guide. Generally, the thickness of the nerve block guide is of from about 1 mm to about 3 mm though in further embodiments may be thicker or thinner. In further embodiments, tabs, structures, or different ergonomic features may be attached to nerve block guide 24 to assist in holding and maintaining nerve block guide 24 in a proper orientation. As such, a variety of embodiments may be utilized in providing more control over the tissue and better sight reference in forming the multiple nerve block guides of the present invention.

Figure 4A:
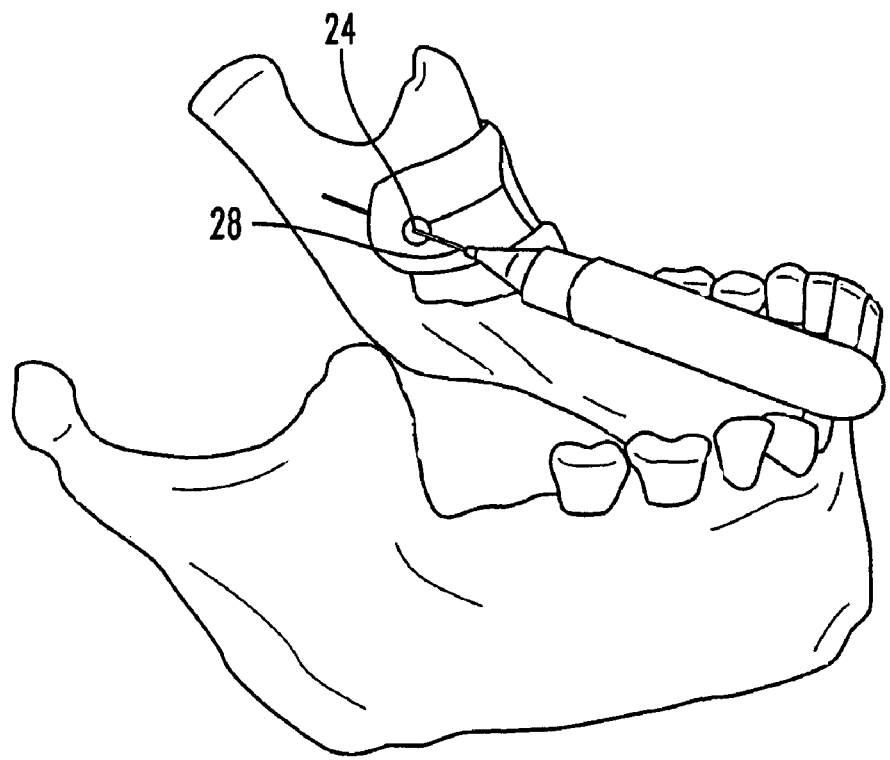
FIG. 4a comprises a perspective side view of one embodiment of a nerve block guide with a needle passing therethrough in relation to a mandible.
Figure 4B:
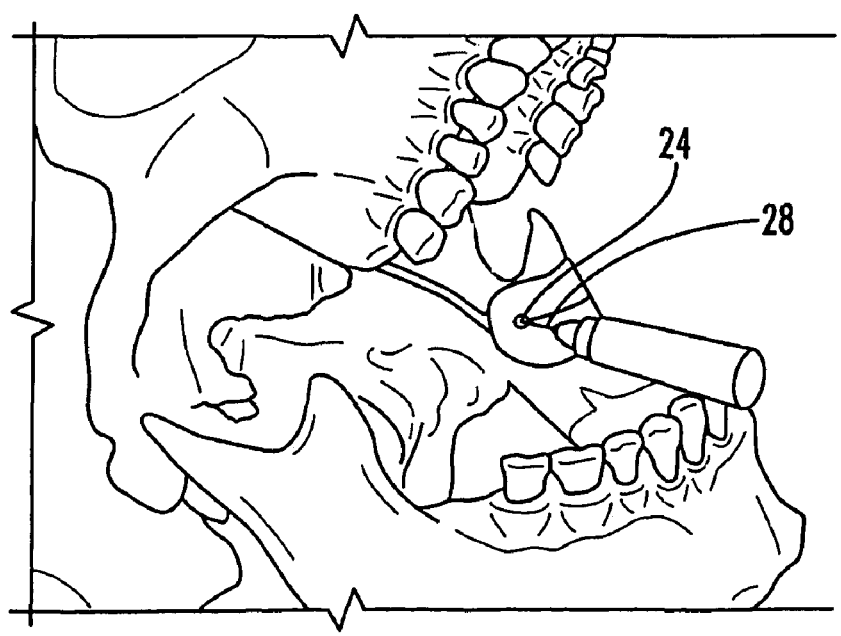
FIG. 4b comprises one embodiment of the nerve block guide of the present invention with a needle passing therethrough in relation to a mandible connected to a skull.

Referring now to FIGS. 4a and 4b, there are illustrations of nerve block guide 22 positioned on mandible 10 with needle 28 situated within needle indexing guide 24 to provide a representation of the orientation of the needle to the desired location on the mandibular foramen 20 in administering anesthesia to block the inferior alveolar nerve. As is illustrated in FIG. 4a, nerve block guide 22 provides for improved control and better sight reference as to where to place the injection as nerve block guide 22 is contoured to fit preferably in a certain arrangement about mandible 10. As such, the repeatability and predictability of the injection point is improved so that a more precise injection may occur to reduce the failure rate in attempts to block the inferior alveolar nerve. Furthermore, FIG. 4b illustrates mandible 10 in connection with the other bones of a human skull so as to generally illustrate how nerve block guide 22 would be utilized for a patient.

Preferably, in administering an injection, standard accepted protocols may be utilized in conjunction with the nerve block guide of the present invention, the nerve block guide placed about the anterior border of the ramus of the mandible in a curve preferable the most concave portion leading to the coronoid process. The practitioner would then maintain the nerve block guide in place to depress the pterygo-mandibular raphe to stabilize the tissue, and thus would insert the needle through a needle indexing guide on the nerve block guide to allow insertion of the needle at the mandibular foramen. After aspiration, anesthesia could then be deposited at the location immediately before the inferior alveolar nerve enters the mandibular foramen.

Accordingly, by the practice of the present invention, the nerve block guide having heretofore unrecognized characteristics is disclosed. The nerve block guide of the present invention provides for improved control and precision in administering injections of anesthesia to block the inferior alveolar nerve. As such, the nerve block guide of the present invention is uniquely affective for dental application where anesthesia should be applied to block the inferior alveolar nerve.

The disclosures of all cited patents and publications referred to in this application are incorporated herein by reference.

The above description is intended to enable the person skilled in the art to practice the invention. It is not intended to detail all of the possible variations and modifications that will become apparent to the skilled worker upon reading the description. It is intended, however, that all such modifications and variations be included within the scope of the invention that is defined by the following claims. The claims are intended to cover the indicated elements and steps in any arrangement or sequence that is effective to meet the objectives intended for the invention, unless the context specifically indicates the contrary.

What is claimed is:

1. A guide for administering an injection of anesthesia in the vicinity of an inferior alveolar nerve of a human comprising:
   a guide body contoured for a human mandible, the preformed guide body having a surface for contacting the human mandible, the surface having a curvature only shaped to an anterior border of a ramus of the human mandible with the guide body shaped to fit at the mandible's coronoid process; and
   at least one needle indexing guide on the guide body for the insertion of a needle there through for the administration of anesthesia in the vicinity of the inferior alveolar nerve.

2. The guide of claim 1 wherein the guide body comprises polymer.

3. The guide of claim 1 wherein the guide body is comprises a material selected from the group consisting of polymers, plastics, thermoplastics, metals, alloys and combinations thereof.

4. The guide of claim 1 wherein at least one needle indexing guide comprises an orifice.

5. The guide of claim 1 wherein at least one needle indexing guide comprises a slot.

6. The guide of claim 1 further comprising the guide body comprising three needle indexing guides.

7. The guide of claim 6 wherein at least two of the needle indexing guides are from about 10 mm to about 15 mm apart.

8. The guide of claim 6 wherein the three needle indexing guides are spaced from about 12 mm to about 13 mm to about 14 mm.

9. The guide of claim 1 wherein the guide body is from about 15 mm to about 20 mm in length.

10. The guide of claim 9 wherein the guide body is about 18 mm in length.

11. The guide of claim 9 wherein the guide body is about 18 mm in width.

12. The guide of claim 1 wherein the guide body is from about 15 mm to about 22 mm in width.

13. The guide of claim 1 wherein the guide body is up to about 3 mm in thickness.

14. The guide of claim 13 wherein the guide body is from about 1 mm to about 3 mm in thickness.

15. A nerve block guide for administering an injection of anesthesia in the vicinity of a inferior alveolar nerve of a human comprising:
   a preformed curved guide body having a surface for contacting the human mandible, the surface having a curvature that is only contoured to the anterior border of the ramus of a mandible with the curved guide body shaped to fit the most concave portion of the anterior border of the ramus of the mandible leading to the coronoid process;
   the curved guide body also for depressing the pterygomandibular raphe of a human prior to the injection; and
   at least one needle indexing guide on the guide body for the insertion of a needle there through to deposit anesthesia at a location immediately before the inferior alveolar enters the mandibular foramen.

16. A method of administering an injection to a human comprising the steps of:
   a) placing a nerve block guide with a guide body contoured for a human mandible, the guide body having a shape and curvature generally shaped to fit the most concave portion of an anterior border of the ramus leading to the mandible's coronoid process; and
      the nerve block guide having at least one needle indexing guide;
   b) holding the nerve block guide in place in contact with a mandible and depressing pterygo-mandibular raphe of the human;
   c) inserting a needle in communication with an injectible medium into the at least one needle indexing guide to guide the needle; and
   d) administering the injectible medium at a location immediately before the inferior alveolar enters the human's mandibular foramen.

17. The method of claim 16 wherein the administering of step d) is at a depth of from about 20 mm to about 25 mm.

18. The method of claim 17 wherein the administering of step d) is at a depth of from about 20 mm to about 23 mm.

19. The method of claim 16 wherein the needle is aspirated prior to step d).

* * * * *